United States Patent [19]

Bower et al.

[11] Patent Number: 5,705,143
[45] Date of Patent: Jan. 6, 1998

[54] BIOLOGICAL TARGETING AGENTS

[75] Inventors: Gary Robert Bower, Aylesbury; Alan Michael Forster, High Wycombe; Anthony Leonard Mark Riley, Marlow; Anthony Eamon Storey, Nr. Amersham, all of United Kingdom

[73] Assignee: Amersham International PLC, Buckinghamshire, England

[21] Appl. No.: 676,263

[22] PCT Filed: Jan. 11, 1995

[86] PCT No.: PCT/GB95/00042

§ 371 Date: Jul. 11, 1996

§ 102(e) Date: Jul. 11, 1996

[87] PCT Pub. No.: WO95/19187

PCT Pub. Date: Jul. 20, 1995

[30] Foreign Application Priority Data

Jan. 12, 1994 [EP] European Pat. Off. ............ 94300224

[51] Int. Cl.⁶ ............................ A61K 51/00; A61M 36/14
[52] U.S. Cl. ........................ 424/1.69; 530/300; 424/1.11; 424/1.65
[58] Field of Search ........................ 424/1.11, 1.65, 424/1.69, 9.1, 9.3, 9.4, 9.5, 9.6; 534/7, 10–14; 530/300, 324–330

[56] References Cited

U.S. PATENT DOCUMENTS

| | | | |
|---|---|---|---|
| 4,479,930 | 10/1984 | Hnatowich | 424/1.11 |
| 4,659,839 | 4/1987 | Nicolotti et al. | 548/546 |
| 4,707,352 | 11/1987 | Stavrianpoulos | 424/1.11 |
| 4,707,440 | 11/1987 | Stavrianopoulos | 435/6 |
| 4,741,900 | 5/1988 | Alvarez et al. | 424/85 |
| 4,980,147 | 12/1990 | Fritzberg et al. | 424/1.11 |
| 5,234,820 | 8/1993 | Wagner et al. | 435/41 |
| 5,276,147 | 1/1994 | Thornback et al. | 534/14 |
| 5,428,139 | 6/1995 | Kiefer et al. | 534/10 |
| 5,428,154 | 6/1995 | Gansow et al. | 540/465 |
| 5,618,513 | 4/1997 | Srinivasan | 424/1.69 |
| 5,635,157 | 6/1997 | Mease et al. | 424/1.53 |

FOREIGN PATENT DOCUMENTS

| | | |
|---|---|---|
| 0 154 788 | 9/1985 | European Pat. Off. |
| 0 515 313 | 11/1992 | European Pat. Off. |
| 2 268 494 | 1/1994 | United Kingdom . |
| WO 93/09816 | 5/1993 | WIPO . |
| WO 93/17719 | 9/1993 | WIPO . |
| WO 93/25244 | 12/1993 | WIPO . |

OTHER PUBLICATIONS

Babich et al., "Technetium–99m–Labeled Hydrazino Nicotinamide Derivatized Chemotactic Peptide Analogs for Imaging Focal Sites of Bacterial Infection," *J. Nucl. Med.* 34:1964–1974 (1993).

Macke et al., "New Octreotide Derivatives for In Vivo Targeting of Somatostatin Receptor–Positive Tumors for Single Photon Emission Computed Tomogrpahy (SPECT) and Positron Emission Tomography (PET)," *Horm. Metab. Res. Suppl.* 27:12 (1993).

*Primary Examiner*—John Kight
*Assistant Examiner*—Dameron Jones
*Attorney, Agent, or Firm*—Marshall, O'Toole, Gerstein, Murray & Borun

[57] ABSTRACT

A conjugate comprises a linear or cyclic synthetic peptide of 3–50 amino acids linked via one of its carboxyl groups and optionally via a linking group, to a polydentate metal chelating group, with the result that endo- or exo-peptidase metabolism of the peptide is substantially inhibited, with the provisos that: a) the peptide chain contains a biological targeting sequence which is biologically active; b) when the spacer is absent the metal chelating group does not comprise solely peptide moieties; c) the metal chelating group does not contain thiol donors. A complex of the conjugate with a metal atom chelated by the metal chelating group is useful in medicine.

8 Claims, 1 Drawing Sheet

Stability of sample in rat kidney homogenate v time

■ Octreotide*    ◆ Somatostatin*    ▲ 99mTc-Compound 4

*Data From Reference 10

BIOLOGICAL TARGETING AGENTS

PRIOR ART

The conjugation of chelating groups to proteins and polypeptides and subsequent complex formation with various radiometals is an established method of radiopharmaceutical design. The chelating group is conventionally attached by reaction of suitable functional groups in the ligand with either amine or thiol groups of the protein. Ligands incorporating such functionality are described as 'bifunctional chelates'.

U.S. Pat. No. 4,479,930 discloses that DTPA bis anhydride can be used to attach DTPA to proteins or polypeptides. The acid anhydride group is ring-opened by the protein amine groups to generate the ligand in situ. DTPA-protein conjugates are not ideal for technetium labelling since non-specific binding to the protein is observed, i.e. the ligand is not sufficiently avid for the radiometal. Further developments have led to bifunctional thiol-containing ligands, since thiols have a higher affinity for certain metals (e.g. technetium) than the free $-NH_2$, $-OH$ or $-CO_2H$ groups of the protein backbone.

Various functional groups have been used for conjugation to the protein amine or thiol groups and include:

| active ester | e.g. US 4897255 |
|---|---|
| isothiocyanate | |
| maleimide | e.g. US 4659839 |
| thiolactone | e.g. US 5095111 and US 4434151 |

U.S. Pat. No. 4,741,900 discloses that protein carbohydrate residues can be oxidised to generate aldehyde moieties which can be derivatised with amine-functionalised ligands to give imine-linked conjugates. The imine linkage can be reduced to an amine to increase stability.

U.S. Pat. No. 5,234,820 discloses site-specific labelling of proteins/peptides at the C-terminus using peptidases, with the emphasis on protein labelling. The C-terminus is said to be useful as a site remote from the active site of the protein. Example 10 makes clear that the basis of the invention is transamidation, i.e. the terminal amino acid is exchanged (e.g. for a labelled one). This is significantly different from simple attachment to a terminal carboxyl group. No chelate conjugates are described.

Recent interest has shifted from high molecular weight proteins or monoclonal antibodies to much smaller peptides as targeting entities for radiopharmaceuticals.

As described above, a range of bifunctional chelating group functionality has been developed for conjugation to protein amine or thiol groups. Custom and practice was therefore to use the same bifunctional ligands to couple to peptide amine groups. This approach is reinforced by conventional solid phase peptide synthetic methods. These normally anchor an amino acid carboxyl group to the resin, leaving the amine group free to react with a second (N-protected) amino acid. Deprotection of the resulting resin-bound peptide permits sequential build up of the desired peptide chain. The resin-bound carboxyl is thus effectively protected, although it is not completely unreactive. For example, treatment of the resin with a strong solution of an organic amine ($RNH_2$ for a prolonged period results in amide formation, i.e. release of peptide-CONHR.

GB 2225579 uses conventional protecting group technology to ensure that the chelating group is attached to the terminal amine of a somatostatin peptide, rather than the lysine residue which is known to be implicated in receptor binding. WO 93/15770 achieves the desired selectivity by control of pH during the conjugation reaction.

WO 91/01144 describes a range of chelate conjugates of peptides, hormones, growth factors, etc. In all cases the ligand is linked to an amine group of the peptide.

Macke et al[19] disclose chelate conjugates of the somatostatin analogue octreotide. Again, the ligands are linked to the peptides via peptide amine groups.

EP 515313 discloses further somatostatin analogues having a variety of chelating groups attached at the terminal amine position of the peptide.

In both WO 91/01144 and GB 2225579 a wide range of spacer groups between the peptide and ligand are claimed, but no particular advantage is shown for any particular linkage.

WO 93/09816 discloses α-emitter conjugates of growth factors for targeting a defined population of cancer cells. The means of conjugation is via a ligand or sequestering agent, with crown ethers being preferred. It is envisaged that the ligand can be attached at either the amine or carboxy terminus of the growth factor with optional use of a linker group. The role of the linker group (p12) is envisaged as the minimisation of steric interactions between the growth factor—α emitter complex and the target. Preferred linkers include disulphides, dicarboxylic acids and modified or unmodified hydrocarbon chains. It is anticipated that the preferred linker will have at least 6 methylene units. The specific disclosure is limited to the radioiodination of EGF (epidermal growth factor), i.e. no chelate-peptide conjugates are actually prepared.

WO 93/17719 discloses ligand-peptide conjugates for forming $^{99m}Tc$ complexes for imaging sites of infection or inflammation. A range of ligands is described including NS bidentates, $N_2S_2$ diaminedithiols or diamidedithiols or $N_3S$ diamidepyridinethiols. The ligands can be attached to an amine or carboxyl group of the peptide with optional use of a linker group. No advantage is shown for any particular site of attachment, linker or ligand.

U.S. Pat. No. 4,707,440 and U.S. Pat. No. 4,943,523 disclose molecules of the form:

[targeting molecule]-LINKER-E-ligand, where E=$-O-$, $-NH-$, or $-S-$ linker=$-NCO-$, $-N=N-$, $-N-$, $-CH_2NH$ ... etc.

Thus, the ligand can be attached to the targeting molecule or polypeptide via a wide array of functionality, but no specific advantage is shown for any particular peptide, linkage or ligand.

Gestin et al.[1] compare the biodistribution in mice of a range of monoclonal antibody (Ab) conjugates of $^{111}In$ complexes of the ligands:

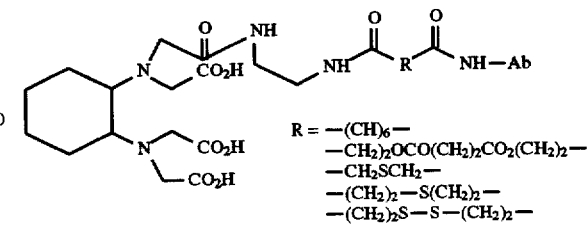

The ligand is attached to the protein amine groups via a mixture of amide and alkylene linkages, with part of the spacer, R, being varied. The conventional wisdom is that metabolisable linkages are useful in improving background clearance of radiolabelled MAbs[2] for example by increased liver clearance. In this case, however, the alkylene $(CH_2)_6$ link gave superior liver clearance. This was ascribed (p770) to a combination of metabolism at the 3 amide linkages in the overall spacer or liver cytochrome P450 degradation of the aliphatic structure.

Yokoyama et al.[3] have studied $^{111}$In complexes of MAb conjugates derived from the ligands:

An alkylene linker gave better tumour uptake than a cleavable diester linkage in a mouse biodistribution study.

Babich et al.[4, 20] have studied $^{99m}$Tc complexes of hydrazone nicotinamide (HYNIC) derivatives of 4 chemotactic peptides for infection imaging. The HYNIC is attached via reaction of a peptide amine group with a HYNIC active ester, except in the case of HP3 (see below) which is carboxyl linked.

| | |
|---|---|
| fNleLFK-HYNIC (HP1) | f = formyl |
| fMLEK-HYNIC (HP2) | Nle = norleucyl |
| fMLFNH(CH$_2$)$_6$NH—HYNIC (HP3) | L = Leu |
| fMLF-D-K-HYNIC (HP4) | K = Lys |
| | M = Met |
| | F = Phe |

Babich et al demonstrate that when the peptide conjugates are unlabelled, HP3 has a marginally better in vitro receptor binding affinity than HP2, which has a lysine (K) amino acid "linker". However, HP2 is more active at inducing superoxide production. The reduced receptor binding affinity of $^{99m}$Tc-labelled HP2 (p1967) compared to unlabelled HP2 implies that technetium labelling has a deleterious effect on binding. No data is given on the binding affinity of $^{99m}$Tc HP3. Babich et al do not investigate the metabolic stability of any of the conjugates, or make any suggestion that advantageous properties are due to carboxyl linking or metabolic stability. Results of in vivo biodistribution experiments do not show any advantage in attaching the HYNIC via a particular group on the peptide. The HYNIC ligand is monodentate leaving the remainder of the metal coordination sphere potentially available for unwanted coordination by the rest of the peptide which is to be labelled.

The Invention

This invention demonstrates that it is possible to attach radiometal complexes to the carboxyl terminus or other carboxyl group of a biologically active peptide without impairment of receptor affinity. Indeed, attachment of the radiometal complex to the C-terminus can have positive benefits in that carboxypeptidase cleavage is blocked hence the peptide is protected from rapid metabolic breakdown (and hence loss of receptor binding affinity). A further advantage is that the biolocalisation properties of such a radiometal-peptide conjugate can be modified so that receptor affinity is at least maintained but background clearance (e.g. liver or kidney excretion) can be increased. This results in a radiopharmaceutical with superior characteristics to those of the parent peptide or targeting entity. This is illustrated below for the case of somatostatin.

The invention provides a conjugate comprising a linear or cyclic synthetic peptide of 3–50 amino acids linked via one of its carboxyl groups and optionally via a linking group, to a polydentate metal chelating group, with the result that endo- or exo-peptidase metabolism of the peptide is substantially inhibited, with the provisos that:

a) the peptide chain contains a biological targeting sequence which is biologically active;

b) when the spacer is absent the metal chelating group does not comprise solely peptide moieties;

c) the metal chelating group does not contain thiol donors.

Preferably, the conjugate has the formula:

[peptide-CONR—(A)$_p$]$_q$—L where:

L is the metal chelating group p is 0 to 10 q is 1 to 3;

A is the same or different and is independently chosen such that

A can be —CR$_2$—

AA can be —(CO)NR—, —NR(CO)— or —CR=CR—

AAA is —CR$_2$QCR$_2$;— where Q=O, S or NR;

R is independently H, C$_{1-6}$ linear or branched hydrocarbon which may be alkyl or one or more of alkenyl; alkoxy; alkoxyalkyl; primary, secondary or tertiary amide; primary, secondary or tertiary amine; hydroxy; hydroxyalkyl; carboxylic acid; aryl or heteroaryl or 2 R groups taken together with the atoms to which they are attached form a carbocyclic, heterocyclic, saturated or unsaturated ring.

Preferred metal chelating groups are tetradentate ligands, such as diaminedioximes of formula:

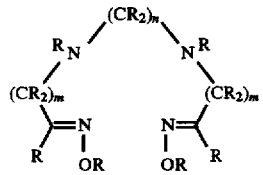

where

R is as defined above n is 2 to 5 m is 1 or 2 with the provisos that:

one or both of the amine groups may be an amide donor;

1 to 3 of the R groups is —(A)$_p$NR(CO)—peptide.

The invention also provides complexes comprising a conjugate as herein described and a metal atom chelated by the metal chelating group.

In another aspect the invention provides complexes as described above for use in medicine.

In a further aspect, the invention provides the use of a conjugate or complex as described herein for the manufacture of a medicament for radioimaging.

The term metal atom is used herein to describe the metal species which may be present in a variety of oxidation states, or even associated with O, OH, Cl etc., depending on its chemistry. The metal species chelated by the ligand is preferably radioactive, although non-radioactive metals may be useful e.g. as contrast agents in n.m.r. in some cases. Preferred radioactive metals include $^{99m}$Tc, $^{186}$Re, $^{188}$Re, $^{67}$Cu and $^{107}$Ag.

Sandostatin (Octreotide) is a synthetic cyclic octapeptide designed to bind to somatostatin receptor sites but with a much longer biological half-life than natural somatostatin (vide infra). Octreotide has been conjugated with DTPA at the terminal amine position and labelled with $^{111}$In as a radiotracer of somatostatin receptors expressed on a number of tumour types[5]. Attempts to label DTPA-octreotide with $^{99m}$Tc have been unsuccessful[6], presumably because the DTPA ligand has insufficient affinity for technetium. GB 2225579 (vide supra) discloses the idea of attaching various other ligands and/or linking groups to the amine terminus of somatostatin analogues.

Macke et al., acknowledged above, disclose $^{67}$Ga and $^{68}$Ga desferrioxamine-octreotide and a $^{99m}$Tc labelled PnAO-octreotide, both linked via the octreotide (D)Phe amine group. Macke et al. imply that the high hepatobiliary excretion of the $^{99m}$Tc-PnAO-octreotide conjugate obviates any advantage which $^{99m}$Tc may have had over the $^{111}$In-DTPA prior art. An alternative interpretation is that these observations are not necessarily intrinsic to the Tc-PnAO complex but the phenyl thiourea linkage used. The lipophilicity conferred by this linkage is probably largely responsible for the unwanted hepatobiliary excretion.

Other attempts at labelling somatostatin or analogues containing Cys—Cys bonds with technetium have used 'direct labelling' methods, i.e. reduction of the disulphide bond either with ascorbic acid[7] or solid reductant[8] to generate free thiol groups for metal coordination. Such cleavage of the peptide disulphide bond upsets the conformation of the polypeptide and results in reduced receptor affinity. Attempts have also been made to attach thiol groups to the amine terminus of somatostatin using the known derivatising agent 2-iminothiolane[9].

Somatostatin-14 (SS-14) is particularly susceptible to metabolism by carboxypeptidases due to its free Cys carboxy terminus[10], but the synthetic analogue Octreotide incorporates a reduced Thr(ol) moiety at the C terminus to block metabolism. The present invention discloses that attachment of a ligand via a suitable linker to the C-terminus of somatostatin analogues gives rise to radiolabelled peptides which both retain their biological activity and are resistant to metabolic cleavage.

The biological activity of these conjugates is surprising in view of previous SAR studies which indicate that the C-terminus of the peptide is relatively sensitive to structural change for the Octreotide analogue shown[10].

D-Phe—Cys—Phe-D-Trp—Lys—Thr—Cys—B   (SEQ ID NO:1)

| B | Relative potency (%) of growth hormone inhibition in vivo* |
|---|---|
| —Phe(ol) | 650 |
| —D-Thr(ol) | 1100 |
| —D-Thr(NH$_2$) | 1160 |
| —Ser(ol) | 2800 |
| —Thr(ol) | 7000 |

*relative to somatostatin = 100%

In the present invention the peptides studied were radiolabelled with either $^{123}$I or $^{99m}$Tc and their biodistributions studied in rats with organs of particular interest being the adrenals and pancreas. This is because somatostatin receptors have been shown in vitro to be enriched in a number of tissues including adrenals[11,12], pancreas[13,14], pituitary[11,14] and brain[15]. Uptake of somatostatin and analogues into adrenals and pituitary have been demonstrated in vivo[16,17,18]. Brain somatostatin receptors are not visualised when the compound is administered in vivo. In this study measurement of pituitary uptake was not sufficiently sensitive to distinguish specific and non-specific effects.

It is envisaged that the role of the linker between the radiometal complex and targeting peptide is to distance the relatively bulky metal complex from the active binding site of the peptide so that receptor binding is not impaired. This can be achieved by a combination of flexibility (e.g. simple alkylene chains) so that the bulky group has the freedom to position itself away from the active site and/or rigidity such as a cycloalkyl or aryl spacer which orientates the complex away from the active site. Non-peptide linkers such as alkylene groups have the advantage that there are no significant hydrogen bonding interactions with the conjugated polypeptide so that the linker does not wrap round onto the peptide. Such a wrap round may adversely affect the preferred conformation of the biologically active sequence of the peptide. This may result from steric interactions with the (relatively large) metal complex, or electronic interactions arising from the electron cloud around the metal. Clearly when the metal complex is charged a more dramatic influence is anticipated.

The linker should also be resistant to metabolic cleavage (especially from peptidases) which would separate the radiolabel from the desired targeting peptide. Hence it is advantageous if simple peptide bonds derived from naturally occurring (L) amino acids are precluded from the linker. Other functionalities which should be excluded from the linker are: ester and disulphide.

A further important characteristic of the linker is that it should not exhibit significant metal co-ordinating ability, i.e. it must not compete effectively with the conjugated ligand for the radiometal. Thus, although heteroatoms such as ether, thioether, amine or amide groups can be incorporated into the linker, these should not be so configured as to give potential 5 or 6 ring chelates upon co-ordination to a metal. Thus peptide linkers are not preferred since these present a string of potential amide donors which would give 5-ring chelates on coordination.

The metal chelating ligand used in the present invention must be able to compete effectively with the polypeptide for the radiometal during the radiolabelling of the chelate-peptide conjugate. This means that the ligand must have more favourable labelling kinetics than the array of amide, carboxyl, amine and possibly thiol donors presented by the targeting polypeptide. Clearly non-specific bonding of the radiometal to the peptide portion of the chelate-peptide conjugate is likely to drastically reduce receptor affinity. Once formed, the radiometal complex must have thermodynamic stability so that the radiometal does not subsequently exchange either with the polypeptide of the conjugate or with endogenous proteins etc. in vivo. The need for stability dictates that the ligand is polydentate and preferably tetradentate.

The metal chelating ligand used should also have the capability to co-ordinate the radiometal at very low ligand concentrations. Such low concentrations are necessary to minimise inhibition of receptor or target uptake by the free chelate-peptide conjugate and/or the conjugate complexed to non-radioactive metals. The need for low concentrations is further exemplified in the case of targeting peptides with profound biological effects to minimise toxicity, e.g. certain N-formyl peptides which target leucocytes but which are also known to cause neutropenia.

Where the desired targeting peptide is cyclic by virtue of one or more disulphide bonds, it is preferable that the ligand does not contain thiol groups. This is because thiols are known to be capable of reducing disulphide bonds to free thiols with the result that the ligand may cause scrambling of the structure and/or active conformation of the targeting peptide with consequent loss of receptor affinity.

The following ligands are expected to be useful in the present invention:

i) Peptides with at least one disulphide bond
Diaminedioximes

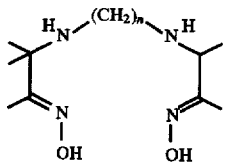

plus variants of the above when one or both of the amines is an amide donor
bis dithiosemicarbazones

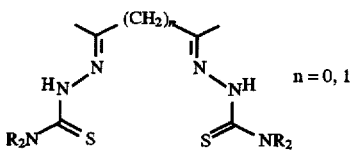

macrocyclic ligands incorporating amine, ether or thioether donors, e.g. cyclam
polyaminocarboxylate ligands such as DOTA, TETA, EDTA, DTPA or IDA
open chain tetraamines ii) peptides without disulphide bonds
All of the ligands discussed in (i) above plus:
$N_2S_2$ and $N_3S$ ligands such as: BAT (Kung, EP 0,200,211 A); ligands described in U.S. Pat. No. 4,925,650 and Brandau et al. J. Nucl. Med., 33, 919 (1992); S-functionalised $N_2S_2$ thioether ligands disclosed in U.S. Pat. No. 4,746,505; the ligands DADS and $MAG_3$ (Fritzberg, U.S. Pat. No. 4,980,147). Also including diaminedithiols, diaminethioetherthiols, diamidedithiols, amideaminedithiols (monoaminemonoamide—MAMA) and triamidethiols.

laminin fragments, e.g. YIGSR (SEQ ID NO:2), PDSGR (SEQ ID NO:3), IKVAV (SEQ ID NO:4), LRE and KCQAGTFALRGDPQG (SEQ ID NO:5)

N-formyl peptides for targeting sites of leucocyte accumulation

PF4 for imaging infection

RGD-containing peptides for targeting platelets

These and other targeting peptides of interest are disclosed in WO 92/13572 (Diatech), EP 527056 (LDV, Antisoma) and WO 92/18534 (EPPT, Antisoma).

REFERENCES

1. J F Gestin et al., Nucl. Med. Biol., 20 763 (1993)
2. S M Quadri et al. J. Nucl. Med. 34 938 (1993) and references therein
3. K Yokoyama et al. ibid. 34 Supplement, P102 and P103 (1993)
4. J W Babich et al. ibid. 34 Supplement, P836 (1993).
5. E P Krenning et al, Metabolism, 41 (Suppl.2) 83 (1992)
6. S J Mather et al. Nucl. Med. Commun. 13, 219 (1992) (oral disclosure)
7. M L Thakur et al. J. Nucl. Med., 33 851 (1992)
8. P H Cox, Eur. J. Nucl. Med., 18, 558 (1991)
9. J K Amartey et al. Nucl. Med. Biol. 20, 539 (1993)
10. J Pless et al. Scand. J. Gastroenterol., 21 (Suppl.119) 54 (1986)
11. J C Reubi et al. Metabolism, 39, 78 (1990)
12. R Maurer et al. Mol. Cell. Endocrinol., 45, 81 (1986)
13. C B Srikant et al. J Biol. Chem., 261, 7690 (1986)
14. J C Reubi et al. Biochem. Biophys. 105, 1538 (1982)
15. J C Reubi et al. Life Sci., 28 2191 (1981)
16. W H Bakker et al. J. Nucl. Med., 31, 1501 (1990)
17. W H Bakker et al. Life Sci., 49, 1593 (1991)
18. J R J Baker et al. Regul. Peptides, 9 213 (1984)
19. H. R. Macke et al. Horm. Met. Res. Suppl., 27, 12 (1993)
20. J. W. Babich et al. J. Nucl. Med., 34, 1964 (1993)

COMPOUND STRUCTURES

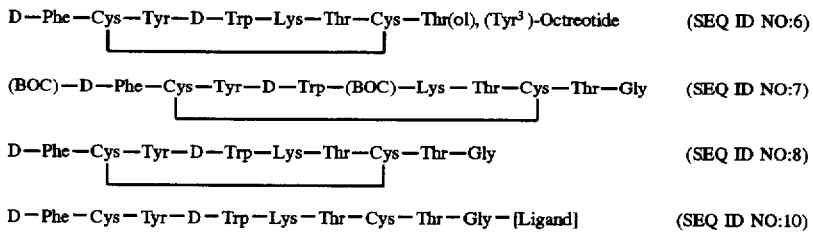

Diaminedioxime ligands are preferred for chelate-peptide conjugates. Firstly, such ligands do not contain thiols and are hence compatible with any peptide. Secondly, they form stable metal complexes with radiometals such as $^{99m}Tc$. Thirdly, PnAO and its amine-functionalised derivative have been shown to successfully label technetium at very low ligand levels ($1-4\times10^{-8}$ mol). This last observation is contrary to the conventional wisdom that thiol donors are the most avid for technetium.

Suitable peptides for use in the present invention include, but are not limited to:

somatostatin, octreotide and analogues for cancer diagnosis 5 (Compound 3)-Ala-Gly-Gly-Gly-[Ligand 7] (SEQ ID NO:10)

6 (Compound 3)—$NH(CH_2)_6CO$—[Ligand 7]

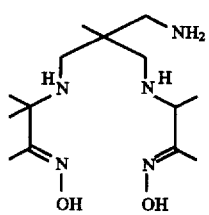

-continued

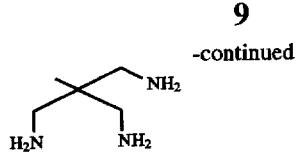

Somatostatin-14 (SEQ ID NO:11)

(S-14)

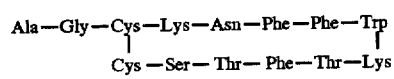

EXPERIMENTAL

Abbreviations tBOC=(tert-butoxy)oxycarbonyl

BOP=Benzotriazolyl-N-oxy-tris(dimethylamino) phosphonium hexafluorophosphate

TFA=trifluoroacetic acid

SS-14=somatostatin

FAB=Fast atom bombardment

DMSO=Dimethylsulfoxide

EXAMPLE 1

Synthesis of Compound 1

Figure 1:
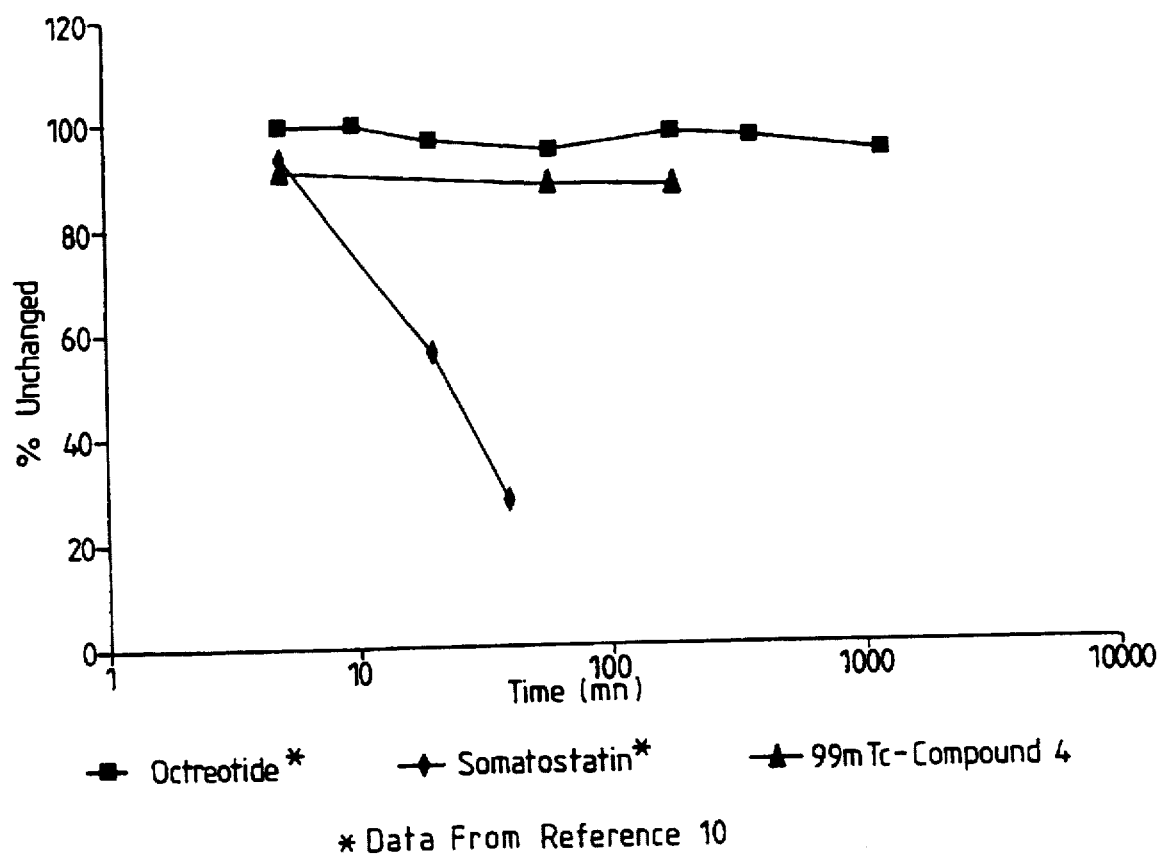
FIG. 1 shows the metabolic stability of $^{99M}$TC-compound 4, octreotide and somatostatin in the presence of rat kidney homogenate.

This peptide was synthesised by standard methods of solid phase synthesis using a $^t$BOC strategy for amine protection.

The product was characterised by mass spectroscopy (FAB) and shows a $(M+H)^+$ peak at 1035.5 (Theoretical= 1035.5). HPLC analysis (System A) shows 95% purity ($R_f$=9.1 mins).

EXAMPLE 2

Synthesis of Compound 2

Compound 2 was synthesised using standard solid phase methods.

The product was characterised by FAB-mass spectroscopy and shows a $(M+H)^+$ peak at 1306.2 (Theoretical= 1306.5). HPLC analysis shows a peak at 8.92 minutes (95% purity) (System B).

EXAMPLE 3

Synthesis of Compound 3

This was prepared by deprotection of Compound 2 with TFA/H$_2$O (95:5).

EXAMPLE 4

Synthesis of Compound 4

This was prepared by BOP coupling of Compound 2 and Compound 7 in DMSO followed by deprotection using TFA/H$_2$O (95:5). The product was purified by HPLC (System C) to give a single peak at 14.4 minutes of 99+% purity. FAB-MS of the product showed $(M+H)^+$ at 1404.0 (Theoretical=1403).

EXAMPLE 5

Synthesis of Compound 5

BOC-Ala-Gly-Gly-Gly (SEQ ID NO:10) was coupled to Compound 7 using BOP and then deprotected using TFA. The Ala-Gly-Gly-Gly—Compound 7 was then coupled to Compound 2 using BOP, deprotected using TFA and HPLC purified. HPLC analysis (System D) showed a purity of 98%. Electrospray mass spectroscopy showed two major peaks, one at 549.8 and one at 824.0 corresponding to:

$$\frac{[M+3H]^+}{3} \text{ and } \frac{[M+2H]^+}{2}$$

This gives an experimental molecular mass of 1646.2 (Theoretical=1645.7).

EXAMPLE 6

Synthesis of Compound 6

This was prepared by coupling BOC-6-aminohexanoic acid to Compound 7 using BOP and deprotecting with TFA. This was then coupled to Compound 2 using BOP, deprotected with TFA and purified by HPLC. Electrospray mass spectroscopy of the product showed 2 major peaks at 506.85 and 769.51 corresponding to:

$$\frac{[M+3H]^+}{3} \text{ and } \frac{[M+2H]^+}{2}$$

to give an experimental molecular mass of 1517.3 (Theoretical=1516.8).

EXAMPLE 7

Synthesis of Compound 7

Compound 8 (22.76 g, 194 mmol) was mixed with 2-chloro-2-methyl-3-nitrosobutane (51.49 g, 0.38 mmol) in dry methanol (120 ml) at 0° C. The mixture was stirred for 15 minutes than allowed to warm to room temperature. It was then heated to 60° C. when an exothermic reaction took place. The reaction was allowed to stir at room temperature for 72 hours, refluxed for a further 3 hours then the solvent removed by rotary evaporation. The residue was dissolved in 2M HCl (200 ml) and washed with diethyl ether (3×200 ml). The aqueous layer was basified to pH 10.0 with 6M sodium hydroxide and extracted with dichloromethane. On standing overnight, crystals separated out, from this and the aqueous layer.

Analysis: C,H,N Expected 57.9%, 10.55%, 22.21% Observed 56.77%, 10.38%, 22.15% $^1$H NMR (CDCl$_3$) δ (ppm) 0.8 (3H, s, CCH$_3$), 1.2 (12H, s, C(CH$_3$)$_2$), 1.8 (6H, s, H$_3$CC=N) 2.35 (4H, q, CH$_2$NH), 2.8 (2H, s, CH$_2$NH$_2$)

EXAMPLE 8

Synthesis of 2-(Aminomethyl)-2-methyl-1,3-diaminopropane (Compound 8)

This was synthesised from the corresponding triol via conversion to the trimesylate, nucleophilic displacement of the mesylate groups by azide (CAUTION) and reduction with hydrogen/palladium catalyst to the triamine.

EXAMPLE 9

HPLC

System A:
 Column: Nucleosil C-18 150×4.6 mm
 Flow: 1.2 ml min$^{-1}$
 Detection: UV 210 nm
 Eluant A: 0.1% aqueous triethylammonium phosphate
 Eluant B: Acetonitrile
 Gradient: 5 to 65% B over 20 minutes
System B:
 As System A but Gradient=40 to 100% B over 20 minutes.
System C:
 Column: HICHROM RP8 250×10 mm
 Flow: 2.5 ml min$^{-1}$
 Detection: UV 215 nm
 Eluant A: 0.1% triethylamine acetate pH 4.5
 Eluant B: Acetonitrile
 Gradient: 0 to 10% B over 2 min 10% B for 5 min
  10 to 50% B for 3 min 50% B for 5 min
  50 to 80% B over 3 min 80% B for 5 min
System D:
 As System A but Gradient=10 to 60% B over 25 minutes.

EXAMPLE 10

Iodine-123 Labelling of Peptides and Compounds 1, 3, 4, 5 and 6

Peptides were labelled with $^{123}$I using the chloramine-T method. A solution of the peptide (20 µg in 20 µl water) was mixed with phosphate buffer (pH 7.4, 0.5M, 100 µl), then carrier-free Na$^{123}$I solution (in 0.02M NaOH solution, 200–400 MBq, 20–100 µl) and then chloramine-T solution (0.2 mg/ml in H$_2$O, 20 µl) and incubated at RT for approx. 30 seconds. The iodination reaction was terminated using saturated aqueous L-Tyrosine solution (20 µl).

The crude labelled peptide was purified from unlabelled peptide and iodination by-products by HPLC (method described below). HPLC purified material was collected in silanised, 10 ml P6 vials. The fraction containing the desired iodinated peptide was evaporated in vacuo at ambient laboratory temperature to remove organic HPLC eluent and then diluted with phosphate buffer (0.2M, pH 7.4) to provide approximately 2 ml of a solution with suitable pH for biological testing.

The radiochemical purity (RCP) of the purified iodinated peptides was assessed by HPLC (method described below) as soon as possible before and after animal injections.

EXAMPLE 11

Carrier Effect on $^{123}$I—Compounds 1 and 6

For $^{123}$I—Compounds 1 and 6 the effect of carrier peptide on the biodistribution of the carrier-free $^{123}$I peptide was assessed by preparing 2 ml of a phosphate buffered solution of HPLC-purified carrier-free iodinated peptide as described above but then subdispensing 1 ml of this solution into a second vial containing carrier peptide. The level of carrier peptide added (1.5 to 2×10$^{-8}$ moles) was comparable to that of carrier peptides in Tc labelled preparations, see below. The presence of this level of carrier peptide significantly reduced uptake of the radioiodinated peptide into receptor tissue in vivo.

A similar 'carrier-effect' is anticipated for technetium labelled peptides, therefore the only valid comparison of biodistribution data for $^{99m}$Tc and $^{123}$I labelled peptides is when both are carrier-added (CA).

EXAMPLE 12

$^{99m}$Tc Labelling of Compounds 3, 4, 5 and 6

A solution of the peptide in MeOH or H$_2$O (1.2 to 3.6×10$^{-8}$ mole) was transferred to a N$_2$ filled 10 ml P6 vial followed by 1 ml of deoxygenated saline (0.9% w/v) and 20 µl aqueous NaOH (0.1M). To this solution was added 1 ml of technetium-99m generator eluate (approximately 0.2 GBq) and then 0.1 ml (10 µg) aqueous SnCl$_2$ solution. The labelling pH was 9.0–10.0. Vials were incubated at ambient laboratory temperature for 1 to 2 hours to effect labelling. No HPLC purification was performed.

EXAMPLE 13

Characterisation and Purification Methods

Iodinated peptides

The radiochemical purity (RCP) determination and purification of iodinated peptides was carried out using the following HPLC systems:

Compounds 1 and 3–6
 Column: C18 Nova-Pak 150×3.9 mm, 4 µm packing
 Gradient: 10–70% B in 20 min
 Eluent A: 0.1% TFA in H$_2$O
 Eluent B: 0.1% TFA in acetonitrile
 Flow rate: 1 ml/min
Somatostatin-14 (SS-14)
 Column: Nova-Pak C18 150×3.9 mm, 4 µm packing
 Gradient: T$_o$ 25% B T$_5$. 30% B T$_{25}$. 40% B Eluents A and B, flow rate and active peak detection are as outlined above.

Iodine-123 species and carrier peptides were detected using in line γ and UV detection, respectively. (UV detector set to λ=215 nm). Solvent control was achieved using Gilson Gradient Manager software.

The RCP data for preparations submitted for animal testing are given in Table 1.

TABLE 1

| | RCP | | | | |
|---|---|---|---|---|---|
| | Pre-Animal Test | | | Post-Animal Test | |
| $^{123}$I SS-14 (CF) | 1 hr 24' | 16.7' | 95% | 2 hr 12' | 16.7' | 95% |
| $^{123}$I-Cmpd. 1 (CA) | 1 hr 7' | 13.2' | 86% | 2 hr 24' | 13.1' | 86% |
| $^{123}$I-Cmpd. 1 (CF) | — | — | — | 1 hr 51' | 13.2$^1$ | 82% |
| $^{123}$I-Cmpd. 3 (CF) | 1 hr 33' | 13.6' | 92% | 2 hr 10' | 13.6' | 92% |
| $^{123}$I-Cmpd. 4 (CF)* | — | — | — | 2 hr 20' | 14.3' | 80% |
| $^{123}$I-Cmpd. 5 (CF) | 1 hr 2' | 13.2' | 97% | 2 hr 2' | 13.2' | 95% |
| $^{123}$I-Cmpd. 6 (CA)* | — | — | — | 2 hr 4' | 14.85'/15.9' | 84% |
| $^{123}$I-Cmpd. 6 (CF)* | — | — | — | 2 hr 39' | 15.0'/16.3' | 90% |

CA = carrier added, see Example 11
CF = carrier free, see Example 11
*Mixture of mono-and di-iodo peptide $^{99m}$Tc labelled peptides Radiochemical purity was assessed using the thin layer chromatography (TLC) and HPLC systems described below.
TLC:
 i) ITLC SG 2 cm×20 cm eluted with 0.9% w/v saline
 ii) ITLC SG 2 cm×20 cm eluted with butan-2-one
 iii) Whatman No. 1 2 cm×20 cm eluted with 50:50 v/v acetonitrile: H$_2$O ITLC SG=instant thin layer chromatography, silica gel impregnated sheets supplied by Gelman.

The labelled species remain at, or close to, the origin in TLC systems (i) and (ii) and moves close to the solvent front in system (iii).

HPLC: Column: Hamilton PRP-1 150×4.1 mm 10 µm packing

Gradient: Elution profile 0–100% B in 17

Eluent A: pH 5.6 50 mM acetate buffer

Eluent B: Tetrahydrofuran unstabilised

Flow rate: 2 ml/min $^{99m}$Tc species were detected using in line γ detection.

RCP data for $^{99m}$Tc-labelled compounds 3, 4, 5 and 6 are outlined below in Table 2.

concentration is the proportion of total activity in the organ divided by the proportion of bodyweight comprised by the organ. Thus, if a compound is uniformly disseminated throughout the body according to tissue weight then a given organ will have a relative concentration=1. A relative concentration>1 implies sequestration and/or retention of the compound and is a useful index where the absolute uptake (% injected dose per organ) is low.

Organs in which the test agent were looked for included the adrenals and the pancreas, where somatostatin receptors are known to be enriched (vide supra). A summary of the biodistribution data is given in Table 3.

TABLE 2

| | | | | | RCP | | |
|---|---|---|---|---|---|---|---|
| | | TLC | | | | HPLC | |
| Compound 3 (CA) | 1 hr 15' | 94% | 2 hr | 96% | 1 hr 16' | 9.5'(44%) 8.5'(28%) 8.1'(26%) | } 7.8' sh |
| | | | | | 2 hr 4' | 9.5'(46%) 8.5'(21%) 8.1'(31%) | } 7.8' sh |
| Compound 4$^{(a)}$ (CA) | 1 hr 37' | 83% | 2 hr 40' | 82% | 1 hr 39' | 9.0'(100%) | 8.8' 8.2' } sh |
| | | | | | 2 hr 47' | 9.1'(100%) | 8.8 8.3 } sh |
| Compound 5 (CA) | 1 hr | 92% | 2 hr 46' | 86% | 1 hr | 9.9'(47%) 9.0'(53%) | } 8.6' sh |
| | | | | | 2 hr 39' | 9.9'(55%) 9.0'(45%) | } 8.6' sh |
| Compound 6 (CA) | 1 hr 20' | 75% | 2 hr 44' | 84% | 1 hr 18' 2 h 46' | 9.5'(96%) 9.5'(98%) | |

$^{(a)}$Preparation filtered; sh = shoulder; CA = carrier-added.

Major impurity in each preparation is reduced hydrolysed technetium.

EXAMPLE 14

Competitive Labelling of PnAO and Compound 3 with Technetium-99m

Solutions of PnAO (3×10$^{-8}$ mole, 8 µg in 8 µl MeOH) and Compound 3 (3.6×10$^{-8}$ mole, 40 µg in 40 µl H$_2$O) were transferred to a N$_2$ filled P6 vial followed by 1 ml of deoxygenated saline (0.9% w/v) and 20 µl aqueous NaOH (0.1M). To this solution was added 1 ml of technetium generator eluate (0.2 GBq) followed by 0.1 ml aqueous SnCl$_2$ (10 µg). The pH of the labelling solution was 9.0.

The RCP of the labelling mixture (measured by the TLC and HPLC systems described above) showed evidence of only $^{99m}$Tc-PnAO.

EXAMPLE 15

Biodistribution in Rats

Male Wistar rats were injected intravenously, under light anaesthesia with the test agent. At 2 minutes, 1 hour and 4 hours post-injection animals were sacrificed by cervical dislocation and various organs and tissue samples were removed for assay of radioactive content. The percentage injected dose in all dissected organs was calculated. In addition the % dose/gram tissue and the relative concentration of activity was calculated for selected organs. Relative

EXAMPLE 16

Metabolic Stability

Rat brain and kidney homogenates were produced by homogenising brain (1.71 g) and kidneys (2.41 g) in 10 vols phosphate buffered saline and centrifuging at 2000 rpm for 5 minutes.

Compound 4 (50 µg) was radiolabelled by stannous reduction of $^{99m}$TcO$_4$$^-$ (0.2 GBq) at pH 9.0.

$^{99m}$Tc-Compound 4 solution (200 µl) was mixed with phosphate buffered saline (800 µl, control) rat kidney homogenate (800 µl) and rat brain homogenate (800 µl) and incubated at 37° C. HPLC analyses using the system described in Example 13 for $^{99m}$Tc labelled peptides were performed on each sample at approx. 1 and 3 hours postmixing.

The chromatograms show little difference between the original labelled Compound 4, the diluted control and the homogenate samples. There is minimal decomposition at 3 hrs of the kidney sample compared with controls.

Discussion

In summary, using adrenal and pancreatic uptake and retention as indicators of somatostatin receptor affinity and metabolic stability it can be seen that use of a flexible linker which is not subject to peptidase cleavage between the peptide and radiometal complex dramatically increases the receptor retention of the radiolabel. Thus, $^{99m}$Tc-Compound 6 exhibits excellent adrenal and pancreas uptake and retention whereas direct linking ($^{99m}$Tc-Compound 4) or use of a metabolisable tetrapeptide spacer ($^{99m}$Tc-Compound 5) show markedly reduced retention of activity. The metabolic stability of $^{99m}$Tc-Compound 4 was further studied in vitro in rat kidney homogenate (Example 16). The results are shown in FIG. 1. It can be seen that the $^{99m}$Tc-compound shows metabolic stability comparable to Octreotide (where the carboxy terminus has been blocked by reduction to an alcohol), whereas somatostatin is rapidly metabolised.

From Table 3 it can be seen that somatostatin receptor binding of $^{123}$I-SS14 can be detected in the adrenal glands and pancreatic tissue. Some differences between adrenal and pancreatic relative concentration of the tracer may be due to the presence of different receptor subtypes in the tissue. Alternatively, the value for uptake in the pancreas may contain a degree of uncertainty due to greater difficulty in delineating the tissue during dissection.

It can be seen that there was marked SS-like binding of $^{123}$I-SS14 at 2 minutes post-injection (p.i.), but this activity was not retained at 1 and 4 hours p.i. $^{123}$I-Compound 1, which is known to have greater in vivo stability, shows SS binding at 2 min and 1 hour p.i., decreasing at 4 hours. Addition of carrier peptide decreases SS receptor binding in the adrenals by 50–60%.

$^{123}$I-Compound 3 shows SS receptor binding activity at 2 min p.i., however this was not maintained at 1 and 4 hours. As $^{123}$I-Compound 3 has an unprotected carboxy-terminus, it was thought that the decrease in binding at 1 and 4 hours was, as in the case of SS-14, due to in vivo metabolism by carboxy-peptidases. This is reflected in the increased level of free iodine produced in vivo and taken up by the thyroid at 4 hours p.i.

Compound 3 can be technetium labelled, but the Tc-Compound 3 shows no specific receptor binding activity, suggesting that direct labelling of the peptide may disturb the binding epitope.

I-Compound 4 shows markedly decreased binding despite the stabilisation of the carboxyterminus of the peptide. The Tc-labelled Compound 4 also shows little specific binding activity. This is thought to be due to steric hindrance of SS receptor binding by the technetium chelating moiety.

Inclusion of a linker between the peptide and the chelate restores SS receptor binding activity to I-Compound 5 and I-Compound 6. Both compounds showed initial uptake comparable to I-SS14 and I-Compound 1, whereas the retention at 1 and 4 hours p.i. is probably greater than that of I-Compound 1.

However, Tc-Compound 5 uptake in adrenals shows no evidence of SS binding activity, despite the I-Compound 5 having a relatively high adrenal and pancreas % injected dose. As the linker in Compound 5 is a tripeptide it is possible that the technetium and chelating moiety are cleaved from the binding peptide in vivo. It is unlikely that free technetium is liberated from the chelate as there is no evidence of pertechnetate uptake by the thyroid.

Use of a less labile linker in Compound 6 appears to stabilise the peptide-chelate against this in vivo metabolism such that Tc-Compound 6 is probably decreased by the presence of carrier Compound 6 present in the preparation. When a comparable amount of carrier is added to the I-Compound 6, the same amount of activity is recovered in the adrenals and pancreas as for the technetium-labelled Compound 6.

TABLE 3

| | | % Injected dose (Relative concentration) | | | | | | |
|---|---|---|---|---|---|---|---|---|
| Compound | Time pi | Adrenal | Pancreas | Blood | Kidney, Bladder & Urine | Liver | Gut | Thyroid |
| I-SS14 | 2 min | 0.19 (7.6) | 2.3 (4.5) | 16.2 | 3.4 | 7.2 | 9.9 | 0.11 |
| | 1 hr | 0.01 (0.4) | 0.3 (0.6) | 5.5 | 9.9 | 2.2 | 19.9 | 1.10 |
| | 4 hr | 0.01 (0.3) | 0.2 (0.4) | 6.1 | 17.9 | 2.4 | 12.1 | 2.00 |
| I-Cmpd 1 CF | 2 min | 0.19 (8.0) | 2.4 (4.8) | 13.1 | 6.3 | 22.3 | 10.6 | 0.09 |
| | 1 hr | 0.15 (6.4) | 0.9 (1.6) | 1.5 | 22.4 | 3.5 | 57.9 | 0.18 |
| | 4 hr | 0.08 (3.1) | 0.7 (1.2) | 1.7 | 22.0 | 1.2 | 56.3 | 0.61 |
| CA | 1 hr | 0.02 (0.8) | 1.2 (2.5) | 1.1 | 21.2 | 3.2 | 62.7 | 0.25 |
| I-Cmpd 3 CF | 2 min | 0.14 (6.7) | 2.3 (4.3) | 16.8 | 6.2 | 17.7 | 8.4 | 0.12 |
| | 1 hr | 0.03 (1.5) | 0.8 (1.0) | 1.9 | 233.2 | 3.3 | 56.1 | 0.09 |
| | 4 hr | 0.02 (0.7) | 0.3 (0.5) | 2.8 | 25.4 | 1.7 | 39.1 | 1.11 |
| Tc-Cmpd 3 CA | 2 min | 0.02 (0.8) | 0.9 (1.6) | 15.4 | 7.6 | 25.3 | 10.3 | 0.07 |
| | 1 hr | 0.00 (0.2) | 0.1 (0.2) | 1.8 | 26.8 | 3.4 | 59.1 | 0.02 |
| | 4 hr | 0.00 (0.1) | 0.0 (0.1) | 0.6 | 23.7 | 1.9 | 70.2 | 0.00 |
| I-Cmpd 4 CF | 2 min | 0.07 (3.0) | 0.9 (1.5) | 18.2 | 10.4 | 24.6 | 6.5 | 0.09 |
| | 1 hr | 0.04 (1.8) | 0.5 (0.8) | 5.0 | 41.6 | 11.6 | 12.1 | 0.34 |
| | 4 hr | 0.02 (0.6) | 0.2 (0.4) | 2.1 | 53.8 | 3.2 | 13.6 | 2.40 |
| Tc-Cmpd 4 CA | 2 min | 0.03 (1.6) | 0.8 (1.4) | 19.4 | 9.0 | 16.8 | 7.0 | 0.12 |
| | 1 hr | 0.01 (0.8) | 0.3 (0.6) | 2.7 | 41.0 | 5.9 | 33.1 | 0.04 |
| | 4 hr | 0.00 (0.4) | 0.1 (0.3) | 0.6 | 42.3 | 2.7 | 47.6 | 0.02 |
| I-Cmpd 5 CF | 2 min | 0.25 (12.3) | 2.8 (4.8) | 14.8 | 6.7 | 21.4 | 9.6 | 0.10 |
| | 1 hr | 0.23 (11.0) | 1.2 (2.1) | 1.9 | 23.0 | 3.1 | 54.7 | 0.30 |
| | 4 hr | 0.10 (2.8) | 0.4 (0.8) | 2.6 | 28.2 | 1.4 | 36.6 | 3.00 |
| Tc-Cmpd 5 CA | 2 min | 0.02 (0.7) | 0.7 (1.0) | 12.7 | 7.6 | 22.7 | 11.0 | 0.10 |
| | 1 hr | 0.00 (0.2) | 0.1 (0.2) | 1.4 | 29.8 | 4.0 | 55.5 | 0.02 |
| | 4 hr | 0.00 (0.0) | 0.0 (0.0) | 0.1 | 26.7 | 2.4 | 68.5 | 0.00 |
| I-Cmpd 6 CF | 2 min | 0.13 (6.3) | 1.2 (2.3) | 13.2 | 13.3 | 29.9 | 6.7 | 0.10 |
| | 1 hr | 0.19 (8.2) | 0.8 (1.6) | 3.5 | 38.9 | 27.5 | 6.9 | 0.12 |
| | 4 hr | 0.10 (3.7) | 0.4 (0.9) | 2.0 | 48.3 | 19.0 | 8.1 | 1.00 |
| I-Cmpd 6 CA | 2 min | 0.05 (2.4) | 1.0 (2.1) | 6.0 | 18.6 | 43.2 | 5.9 | 0.04 |
| | 1 hr | 0.04 (1.8) | 1.0 (1.6) | 2.2 | 28.1 | 51.3 | 5.5 | 0.09 |
| Tc-Cmpd 6 CA | 2 min | 0.04 (1.7) | 0.8 (1.5) | 15.5 | 10.7 | 28.3 | 6.3 | 0.10 |
| | 1 hr | 0.04 (1.6) | 1.1 (1.9) | 3.9 | 38.0 | 12.5 | 22.4 | 0.05 |
| | 4 hr | 0.03 (1.1) | 1.1 (1.9) | 0.8 | 48.9 | 7.4 | 31.4 | 0.03 |

We claim:

1. A conjugate comprising a linear or cyclic synthetic peptide of 3–50 amino acids linked via one of its carboxyl groups and optionally via a linking group, to a polydentate metal chelating group, with the result that endo- or exopeptidase metabolism of the peptide is substantially inhibited, with the provisos that:

a) the peptide chain contains a biological targeting sequence which is biologically active;
   b) when the linking group is absent the metal chelating group does not comprise solely peptide moieties;
   c) the metal chelating group does not contain thiol donors.

2. A conjugate as claimed in claim 1 of formula:

(peptide—(CO)NR—(A)$_p$)$_q$—L where:

L is the metal chelating group
p is 0 to 10
q is 1 to 3;
A is the same or different and is independently selected from the group consisting of —(CR$_2$)—, —(CO)NR—, —NR(CO)—, —CR=CR—, and —CR$_2$QCR$_2$— wherein Q is —O—, —S— or —(NR)—, with the proviso that (A)$_p$ contains a backbone chain of 10 atoms or less;
R is independently H, C$_{1-6}$ linear or branched hydrocarbon which may be alkyl or one or more of alkenyl; alkoxy; alkoxyalkyl; primary, secondary or tertiary amide; primary, secondary or tertiary amine; hydroxy; hydroxyalkyl; carboxylic acid; aryl or heteroaryl or two R groups taken together with the atoms to which they are attached form a carbocyclic, heterocyclic, saturated or unsaturated ring.

3. The conjugate as claimed in claim 1 wherein the metal chelating group is tetradentate.

4. A conjugate as claimed in claim 1 wherein the metal chelating group is a diaminedioxime of formula:

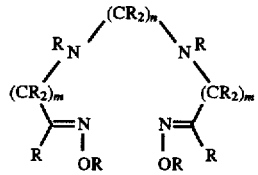

where R is independently H, C$_{1-6}$ linear or branched hydrocarbon which may be alkyl or one or more of alkenyl; alkoxy; alkoxyalkyl; primary, secondary or tertiary amide; primary, secondary or tertiary amine; hydroxy; hydroxyalkyl; carboxylic acid; aryl or heteroaryl or two R groups taken together with the atoms to which they are attached form a carbocyclic, heterocyclic, saturated or unsaturated ring; and
n is 2 to 5
m is 1 or 2
with the provisos that:
one or both of the amine groups may be an amide donor;
1 to 3 of the R groups is —(A)$_p$NR(CO)-peptide and A is the same or different and is independently selected from the group consisting of —(CR$_2$)—, —(CO)NR—, —NR(CO)—, —CR=CR—, and —CR$_2$QCR$_2$— wherein Q is —O—, —S— or —(NR)—, with the proviso that (A)$_p$ contains a backbone chain of 10 atoms or less.

5. A complex comprising a conjugate according to claim 1 and a metal atom chelated by the metal chelating group.

6. A pharmaceutical composition comprising the complex as claimed in claim 5.

7. A method of radioimaging in an animal comprising the steps of complexing the conjugate of claim 1 with a radiometal to form a complex, administering said complex to said animal and detecting the presence of said complex in said animal.

8. A method of preparing a medicament for radioimaging comprising the step of complexing the conjugate of claim 1 with a radiometal.

* * * * *

UNITED STATES PATENT AND TRADEMARK OFFICE
CERTIFICATE OF CORRECTION

PATENT NO. : 5,705,143
DATED : January 6, 1998
INVENTOR(S) : Bower et al.

Page 1 of 4

It is certified that error appears in the above-identified patent and that said Letters Patent is hereby corrected as shown below:

On the title page,

OTHER PUBLICATIONS, at Macke et al., "Tomogrpahy" should be --Tomography--. (Form PTO-1449 filed July 11, 1996)

Column 2, line 61, at the second R= line, "-$CH_2)_2OCO(CH_2)_2CO_2(CH_2)_2$-" should be -- -$(CH_2)_2OCO(CH_2)_2CO_2(CH_2)_2$- --.

Column 5, line 64, "14)" should be --$^{14)}$--.

Column 5, line 66, "18)" should be --$^{18)}$--.

Column 7, lines 6-13,

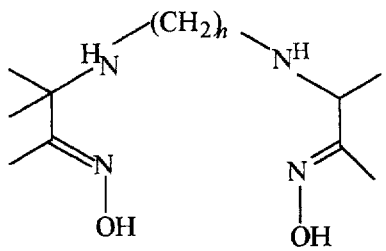

should be

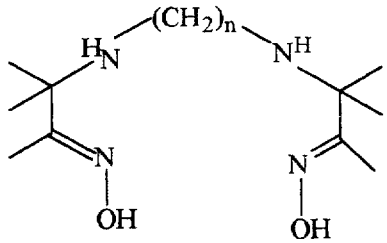

n = 2 EnAO
3 PnAO
4 BnAO
5 PentAO

UNITED STATES PATENT AND TRADEMARK OFFICE
CERTIFICATE OF CORRECTION

PATENT NO.   : 5,705,143                                   Page 2 of 4
DATED        : January 6, 1998
INVENTOR(S)  : Bower et al.

It is certified that error appears in the above-identified patent and that said Letters Patent is hereby corrected as shown below:

Columns 7-8, lines 43-53, at the first compound structure, immediately before "D-Phe..." insert --1--; at the second compound structure, immediately before "(BOC)" insert --2--; at the third structure, immediately before "D-Phe" insert --3--; at the fourth compound structure, immediately before "D-Phe" insert --4--.

Columns 7-8, lines 43-53, at the fourth compound structure
"D-Phe-Cys-Tyr-D-Trp-Lys-Thr-Cys-Thr-Gly-[Ligand]         (SEQ ID NO:10)"

should be

--D-Phe-Cys-Tyr-D-Trp-Lys-Thr-Cys-Thr-Gly-[Ligand 7]         (SEQ ID NO:9)--.

Column 8, line 58, before the structure, insert --7--.

UNITED STATES PATENT AND TRADEMARK OFFICE
CERTIFICATE OF CORRECTION

PATENT NO. : 5,705,143

DATED : January 6, 1998

INVENTOR(S) : Bower et al.

It is certified that error appears in the above-identified patent and that said Letters Patent is hereby corrected as shown below:

Column 8, lines 58-65,

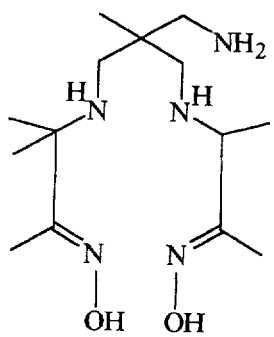

should be

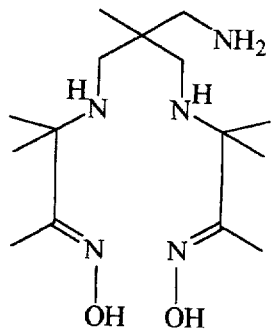

UNITED STATES PATENT AND TRADEMARK OFFICE
CERTIFICATE OF CORRECTION

PATENT NO. : 5,705,143
DATED : January 6, 1998
INVENTOR(S) : Bower et al.

It is certified that error appears in the above-identified patent and that said Letters Patent is hereby corrected as shown below:

Column 9, lines 1-7, before the structure, insert --8--.

Column 9, line 22, "tBOC" should be $^t$Boc--.

Column 10, line 44, "than" should be --then--.

Column 12, line 45, at Post-Animal Test column, "13.2¹" should be --13.2'--.

Columns 15-16, Table 3, before the seventh line of text which reads "CA  1 hr  0.02(0.8)  1.2(2.5)  1.1  21.2  3.2  62.7  0.25" insert the following line: --I-Cmpd 1  2 min  0.08 (3.1)  2.1(4.1)  16.4  3.5  20.5  9.7  0.10--.

Columns 15-16, Table 3, Kidney, Bladder & Urine column, nineth line of text, "233.2" should be --23.2--.

Columns 15-16, Table 3, Gut column, last line of text, "31.4" should be --31.8--.

Signed and Sealed this

Twenty-second Day of August, 2000

Attest:

Q. TODD DICKINSON

*Attesting Officer*   *Director of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: Modified-site
        ( B ) LOCATION: 1
        ( D ) OTHER INFORMATION: /product="D-Phenylalanine"

( i x ) FEATURE:
        ( A ) NAME/KEY: Modified-site
        ( B ) LOCATION: 4
        ( D ) OTHER INFORMATION: /product="D-Tryptophan"

( i x ) FEATURE:
        ( A ) NAME/KEY: Cross-links
        ( B ) LOCATION: 2..7

( x i ) SEQUENCE DESCRIPTION: SEQ ID NO:1:

Xaa  Cys  Phe  Xaa  Lys  Thr  Cys
1                    5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:2:

Tyr  Ile  Gly  Ser  Arg
1                    5

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:3:

Pro  Asp  Ser  Gly  Arg
1                    5

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:4:

Ile Lys Val Ala Val
1               5

( 2 ) INFORMATION FOR SEQ ID NO:5:

( i ) SEQUENCE CHARACTERISTICS:
( A ) LENGTH: 15 amino acids
( B ) TYPE: amino acid
( C ) STRANDEDNESS: Not Relevant
( D ) TOPOLOGY: Not Relevant ( i i ) MOLECULE TYPE: peptide ( x i ) SEQUENCE DESCRIPTION: SEQ ID NO:5:

Lys Cys Gln Ala Gly Thr Phe Ala Leu Arg Gly Asp Pro Gln Gly
1               5                   10                  15

( 2 ) INFORMATION FOR SEQ ID NO:6:

( i ) SEQUENCE CHARACTERISTICS:
( A ) LENGTH: 8 amino acids
( B ) TYPE: amino acid
( C ) STRANDEDNESS: Not Relevant
( D ) TOPOLOGY: Not Relevant ( i i ) MOLECULE TYPE: peptide ( i x ) FEATURE:
( A ) NAME/KEY: Modified-site
( B ) LOCATION: 1
( D ) OTHER INFORMATION: /product="D-Phenylalanine"

( i x ) FEATURE:
( A ) NAME/KEY: Modified-site
( B ) LOCATION: 4
( D ) OTHER INFORMATION: /product="D-Tryptophan"

( i x ) FEATURE:
( A ) NAME/KEY: Cross-links
( B ) LOCATION: 2..7

( x i ) SEQUENCE DESCRIPTION: SEQ ID NO:6:

Xaa Cys Tyr Xaa Lys Thr Cys Thr
1               5

( 2 ) INFORMATION FOR SEQ ID NO:7:

( i ) SEQUENCE CHARACTERISTICS:
( A ) LENGTH: 9 amino acids
( B ) TYPE: amino acid
( C ) STRANDEDNESS: Not Relevant
( D ) TOPOLOGY: Not Relevant ( i i ) MOLECULE TYPE: peptide ( i x ) FEATURE:
( A ) NAME/KEY: Modified-site
( B ) LOCATION: 1
( D ) OTHER INFORMATION: /product="D-Phenylalanine"

( i x ) FEATURE:
( A ) NAME/KEY: Modified-site
( B ) LOCATION: 1
( D ) OTHER INFORMATION: /product="OTHER"
/ note="covalently modified with (tert-butoxy)
oxycarbonyl (BOC)"

( i x ) FEATURE:
( A ) NAME/KEY: Modified-site
( B ) LOCATION: 4
( D ) OTHER INFORMATION: /product="D-Tryptophan"

( i x ) FEATURE:

( A ) NAME/KEY: Modified-site
( B ) LOCATION: 5
( D ) OTHER INFORMATION: /product="OTHER"
/ note="covalently modified with (tert-butoxy) oxycarbonyl (BOC)"

( i x ) FEATURE:
( A ) NAME/KEY: Cross-links
( B ) LOCATION: 2..7

( x i ) SEQUENCE DESCRIPTION: SEQ ID NO:7:

Xaa Cys Tyr Xaa Lys Thr Cys Thr Gly
1               5

( 2 ) INFORMATION FOR SEQ ID NO:8:

( i ) SEQUENCE CHARACTERISTICS:
( A ) LENGTH: 9 amino acids
( B ) TYPE: amino acid
( C ) STRANDEDNESS: Not Relevant
( D ) TOPOLOGY: Not Relevant ( i i ) MOLECULE TYPE: peptide ( i x ) FEATURE:
( A ) NAME/KEY: Modified-site
( B ) LOCATION: 1
( D ) OTHER INFORMATION: /product="D-Phenylalanine"

( i x ) FEATURE:
( A ) NAME/KEY: Modified-site
( B ) LOCATION: 4
( D ) OTHER INFORMATION: /product="D-Tryptophan"

( i x ) FEATURE:
( A ) NAME/KEY: Cross-links
( B ) LOCATION: 2..7

( x i ) SEQUENCE DESCRIPTION: SEQ ID NO:8:

Xaa Cys Tyr Xaa Lys Thr Cys Thr Gly
1               5

( 2 ) INFORMATION FOR SEQ ID NO:9:

( i ) SEQUENCE CHARACTERISTICS:
( A ) LENGTH: 9 amino acids
( B ) TYPE: amino acid
( C ) STRANDEDNESS: Not Relevant
( D ) TOPOLOGY: Not Relevant ( i i ) MOLECULE TYPE: peptide ( i x ) FEATURE:
( A ) NAME/KEY: Modified-site
( B ) LOCATION: 1
( D ) OTHER INFORMATION: /product="D-Phenylalanine"

( i x ) FEATURE:
( A ) NAME/KEY: Modified-site
( B ) LOCATION: 4
( D ) OTHER INFORMATION: /product="D-Tryptophan"

( i x ) FEATURE:
( A ) NAME/KEY: Cross-links
( B ) LOCATION: 2..7

( x i ) SEQUENCE DESCRIPTION: SEQ ID NO:9:

Xaa Cys Tyr Xaa Lys Thr Cys Thr Gly
1               5

( 2 ) INFORMATION FOR SEQ ID NO:10:

( i ) SEQUENCE CHARACTERISTICS:
( A ) LENGTH: 4 amino acids

```
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:10:

Ala  Gly  Gly  Gly
    1

( 2 ) INFORMATION FOR SEQ ID NO:11:

( i ) SEQUENCE CHARACTERISTICS:
        ( A ) LENGTH: 14 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: Cross-links
        ( B ) LOCATION: 3..14

( x i ) SEQUENCE DESCRIPTION: SEQ ID NO:11:

Ala  Gly  Cys  Lys  Asn  Phe  Phe  Trp  Lys  Thr  Phe  Thr  Ser  Cys
    1                  5                         10
```